United States Patent [19]
Gupta

[11] Patent Number: 5,984,946
[45] Date of Patent: Nov. 16, 1999

[54] DIAGNOSTIC AND GUIDING CATHETER

[76] Inventor: Mukesh Gupta, 3713 Sandrock Trail, Owensboro, Ky. 42303

[21] Appl. No.: 09/032,412

[22] Filed: Feb. 27, 1998

[51] Int. Cl.[6] .................................................. A61M 29/00
[52] U.S. Cl. ............................................................ 606/194
[58] Field of Search ................................... 606/191, 192, 606/194, 195, 198

[56] References Cited

U.S. PATENT DOCUMENTS

| | | |
|---|---|---|
| 3,634,924 | 1/1972 | Blake et al. . |
| 3,746,003 | 7/1973 | Blake et al. . |
| 3,995,623 | 12/1976 | Blake et al. . |
| 4,024,873 | 5/1977 | Antoshkiw et al. . |
| 4,522,195 | 6/1985 | Schiff . |
| 4,531,943 | 7/1985 | Van Tassel et al. . |
| 4,601,706 | 7/1986 | Aillón . |
| 4,798,588 | 1/1989 | Aillón . |
| 4,898,577 | 2/1990 | Badger et al. . |
| 4,909,258 | 3/1990 | Kuntz et al. . |
| 4,983,167 | 1/1991 | Schotz . |
| 5,016,640 | 5/1991 | Ruiz . |
| 5,507,770 | 4/1996 | Turk .......................................... 606/198 |
| 5,584,803 | 12/1996 | Stevens et al. .............................. 604/4 |
| 5,749,890 | 5/1998 | Shaknovich .............................. 606/198 |
| 5,766,151 | 6/1998 | Valley et al. .............................. 604/194 |

Primary Examiner—Michael Buiz
Assistant Examiner—Vy Q. Bui

Attorney, Agent, or Firm—Hovey, Williams, Timmons & Collins

[57] ABSTRACT

Diagnostic and guiding catheter assemblies (28, 82) are provided which include an elongated tubular body (30) having a proximal end (32) and a preformed open distal end (34). An expandable distal positioning balloon structure (36) is operatively coupled with the tubular body (30) adjacent to the distal end (34). The tubular body (30) includes wall structure defining a main passageway (48) and a pressurizing tube passageway (46) extending between the proximal and distal ends (32, 34). A pressurizing tube (70) is positioned within the pressurizing tube passageway (46), and is in open communication with the distal balloon interior (66). The pressurizing tube (70) is configured for passing a pressurizing fluid from a source thereof into the distal balloon interior (66) for expanding the distal balloon structure (36). In an expanded state, the distal balloon structure (36) is configured for locating the distal end (34) within a first vessel (18) adjacent to an ostium of a second blood vessel (20), and for positioning the distal end (34) at a selected distance from the second vessel ostium. An alternative catheter apparatus (82) further includes an expandable biasing balloon structure (84) operatively coupled to the exterior of the body (30) between the proximal end (32) and the distal balloon structure (36). The biasing balloon structure (84) is configured for biasing the distal end (34) in a direction toward the second vessel ostium. Selected expansion of the balloon structures (36, 84) allows the physician to precisely position distal end (34) for angiography for PTCA.

18 Claims, 2 Drawing Sheets

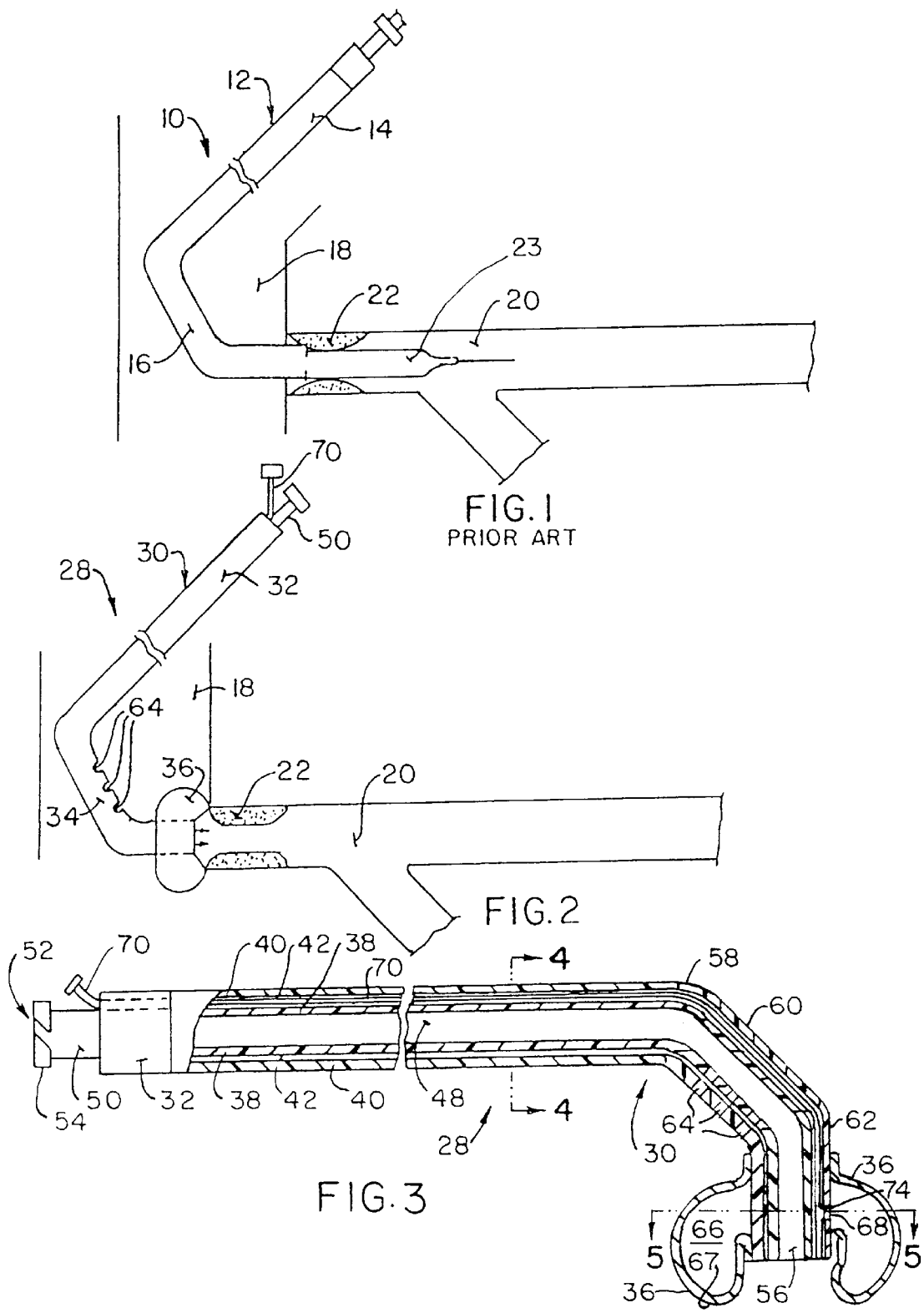

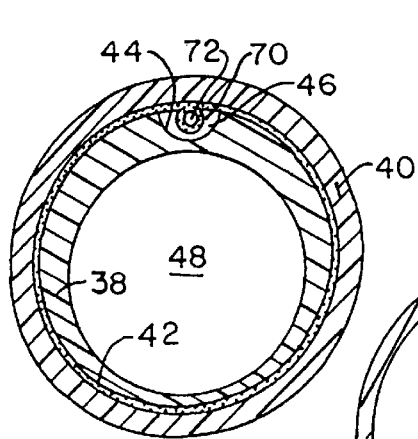
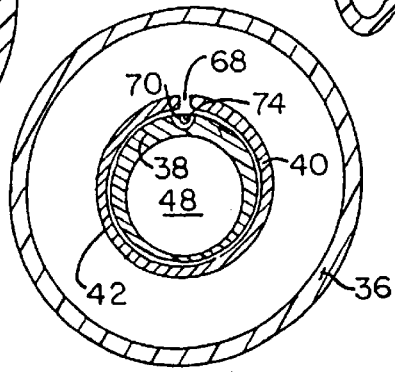
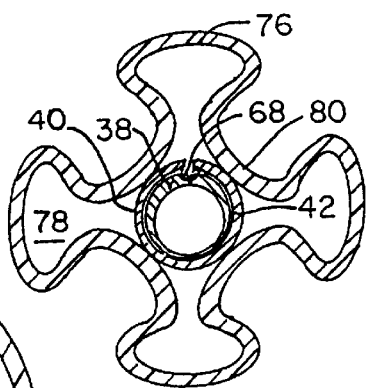
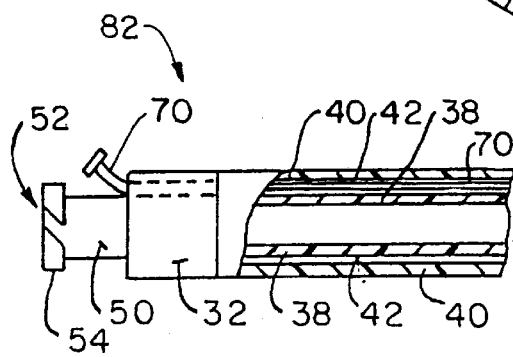
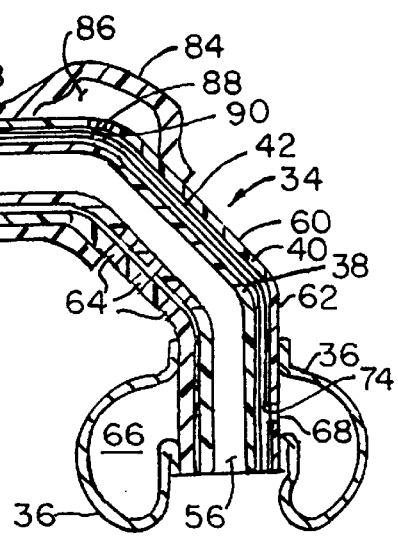

DIAGNOSTIC AND GUIDING CATHETER

BACKGROUND OF THE INVENTION

1. Field of the Invention

The present invention relates generally to surgical devices used in diagnostic testing which include a means for introducing or removing material from a body for therapeutic purposes. More particularly, the invention pertains to a diagnostic and guiding catheter apparatus having a means for precisely locating a distal end of the catheter adjacent to an ostium of a preselected blood vessel, so as to facilitate procedures such as angiography and PTCA.

2. Background of the Prior Art

Many common medical procedures require the insertion of a catheter having a preformed distal end into a patient's cardiovascular system. For example, in selective angiography procedures where an area of a preselected blood vessel is investigated, a coronary diagnostic catheter is percutaneously introduced into the cardiovascular system and advanced therein until the distal tip of the catheter is adjacent the selected area. At this point, radio-opaque contrast is injected into a patient's cardiovascular system, and an X-ray image is taken of the subject area of the blood vessel.

Another procedure involving catheterization is percutaneous transluminal coronary angioplasty (PTCA). In the classic PTCA procedure, a guiding catheter (which is similar in shape to an angiography diagnostic catheter although somewhat stiffer) is percutaneously introduced and moved through the patient's cardiovascular system until the distal tip is adjacent a coronary artery ostium. A guide wire is then introduced through the guiding catheter and is advanced into the patient's coronary vasculature until the distal end of the guide wire crosses the lesion to be dilated. A dilation catheter having an expandable balloon on the distal end thereof is then advanced through the guiding catheter over the previously positioned guide wire until the balloon crosses the lesion. At this point, the balloon is inflated to a predetermined size with radio-opaque contrast solution at relatively high pressures (e.g., 4–12 atmospheres) to compress and split the atherosclerotic plaque of the lesion against the inside of the artery wall to thereby dilate the lumen of the diseased artery. The balloon is then deflated so that the dilation catheter can be removed and blood flow resumed through the dilated artery. Conventional catheters and procedures are described in U.S. Pat. Nos. 4,323,071, 4,439,185, 4,468,224, 4,516,972, 4,538,622, 4,582,185, 4,616,652, and 4,638,805, which are incorporated by reference herein.

It frequently occurs that a coronary stenosis is ostial in location. When the distal tip of a diagnostic or guiding catheter is positioned into the ostiurn of an artery with ostial stenosis, blood flowing into that coronary artery may be drastically lowered or obliterated. This condition requires immediate withdrawal of the distal tip of the catheter in order to prevent development of myocardial ischemia, arrhythmias, hypotension, or even patient death. In such cases, if the patient requires coronary angiography, it is generally performed non-selectively by injecting radio-opaque contrast solution into the ascending aorta. Non-selective coronary angiography requires a larger amount of radio-opaque contrast solution and increases the risks of radio-opaque contrast-induced kidney damage. Moreover, non-selective coronary angiography in general gives a poorer assessment of coronary anatomy.

In cases of ostial stenosis requiring PTCA, it is generally necessary to first position the guiding catheter within the ostium as described. However, in order to allow the dilation balloon to be properly positioned in the ostium, it is normally required that the tip of the guiding catheter be pulled out of the ostial stenosis. That is, without preliminary withdrawal of the guiding catheter tip from the ostium, the dilation balloon may be partially within the confines of the guiding catheter when properly positioned for inflation relative to the lesion. This means that the balloon cannot be fully inflated owing to the mechanical interference presented by the guiding catheter tip. Normally, several balloon dilations are required before an ostial stenosis is satisfactorily dilated, and after each dilation angiography is performed to assess the result of the proceeding balloon dilation. Therefore, PTCA of ostial stenosis requires multiple insertions of the distal tip of the guiding catheter into the ostium of the artery, with subsequent preliminary withdrawal and positioning of the dilation balloon, inflation of the balloon and angiography. With each insertion of the guiding catheter tip into the coronary ostium, the risks of acute coronary closure and myocardial infarction are increased.

Another common problem experienced with prior guiding catheters is their inability to stay in a position when the distal end of a dilation catheter is advanced across a stenosis. Surgeons have attempted to ameliorate this problem by buttressing the guiding catheter against the opposed wall of the aorta, by deep-seating the guiding catheter tip well into the coronary ostium, or by use of guiding catheters of various distal configurations and stiffnesses. These attempted solutions are not always successful and can themselves cause complications. To give but one example, use of various types of catheters requires withdrawal of guiding catheter(s) and replacement thereofwith new catheter(s) having different curvatures or stiffnesses. This recatheterization not only increases the time required for the procedure but may add further arterial trauma. Withdrawal of guiding catheters also necessitate withdrawal of the guide wire and balloon dilation catheter which increases the risk of acute coronary closure and myocardial infarction.

There is accordingly a real and unsatisfied need in the art for improved catheter products which overcome the problems associated with improper guiding catheter tip placement and the tendency of guiding catheters to shift during placement and use of balloon dilation catheters.

SUMMARY OF THE INVENTION

The present invention addresses the problems discussed above, and provides a distinct advance in the state of the art. More particularly, the diagnostic and guiding catheter apparatus hereof includes selectively inflatable means for locating the distal end of the catheter within a first blood vessel adjacent to the ostium of a second, smaller blood vessel in communication with the first vessel in such manner to facilitate angiography, PTCA and other similar procedures.

In a preferred form, a diagnostic and guiding catheter apparatus broadly includes an elongated tubular body presenting a wall structure, and opposed, proximal and distal ends. An expandable distal positioning balloon structure is operatively coupled with the body adjacent to the distal end. The catheter apparatus also includes an expansion means for selectively expanding the distal balloon structure from a point adjacent the proximal end. When the distal balloon structure is expanded, it assumes a configuration providing a means for locating the distal end within the first blood vessel adjacent the second vessel ostium, and for precisely locating the distal end at a selected distance from the second vessel ostium. The distal balloon structure advantageously prevents entry of the distal end deep into the second vessel.

The distal end of the preferred catheter apparatus is substantially hook-shaped. When configured for use as a diagnostic catheter, the distal end may be constructed of a relatively flexible material, such as flexible synthetic resin material. As the distal end of the apparatus is positionable adjacent to the ostium of the second vessel, the apparatus may be used to conduct selective coronary angiography by injecting radio-opaque contrast through the main passageway and into the coronary artery.

When configured for use as a guiding catheter, the distal end is constructed of a relatively rigid material, such as relatively rigid, shape-retaining synthetic resin material. In use as a guiding catheter, the distal end of the apparatus is positioned adjacent to the ostium of the second vessel. The dilation catheter is inserted into the main passageway of the guiding catheter apparatus, and advanced therethrough until the dilation balloon is in the desired position, such as, for example, adjacent to a stenotic obstruction in the second vessel. Inasmuch as the distal balloon structure may be used to precisely position the distal end of the catheter relative to the stenosis, the latter is prevented from interfering with the operation of the dilation catheter.

An alternative catheter apparatus includes an elongated tubular body presenting a wall structure, opposed, proximal and distal ends, and an expandable biasing balloon structure operatively coupled with the tubular body adjacent the distal end in spaced relationship to the extreme tip end of the catheter body. The alternative catheter apparatus is configured to be positioned so that the distal end is located within a first vessel and adjacent to an ostium of a second vessel. The biasing balloon provides a biasing means for biasing the distal end in a direction toward the second vessel ostium, holding the distal end in position. Additionally, selective inflation of the biasing balloon structure during initial placement of the catheter allows alteration in the catheter geometry, thus facilitating easy and precise placement. Finally, the surgeon may selectively inflate the positioning balloon structure and the biasing balloon structure so as to achieve a fully stabilized, precise catheter location.

BRIEF DESCRIPTION OF THE DRAWINGS

FIG. 1 is a fragmentary, generally schematic view showing a prior art guiding catheter device including a tip section positioned within a patient's ascending aorta adjacent to a stenosis within the ostium of a coronary artery, and with a dilation balloon illustrated in phantom disposed across the stenosis and partially within the confines of the tip section;

FIG. 2 is a fragmentary, generally schematic view of the preferred catheter apparatus in accordance with the invention including a tip section positioned within a patient's ascending aorta adjacent to an ostium of a coronary artery;

FIG. 3 is a fragmentary, side view in partial cross-section of the catheter apparatus of FIG. 2;

FIG. 4 is a cross-sectional view taken along line 4—4 of FIG. 3;

FIG. 5 is a cross-sectional view taken along line 5—5 of FIG. 3;

FIG. 6 is a cross-sectional view similar to that of FIG. 5, but illustrating an alternative positioning balloon structure;

FIG. 7 is a fragmentary, side view in partial cross-section similar to that of FIG. 3, but showing an alternative catheter apparatus having an external biasing balloon structure; and FIG. 8 is a fragmentary, generally schematic view of the catheter apparatus of FIG. 7 having a tip section positioned within aorta adjacent to an occluded coronary artery ostium, and with the catheter properly positioned to allow placement and unimpeded use of a dilation balloon within the ostium stenosis.

DETAILED DESCRIPTION OF THE PREFERRED EMBODIMENTS

A conventional diagnostic and guiding catheter 10 positioned within a patient's cardiovascular system is illustrated in FIG. 1. The catheter 10 includes an elongated tubular body 12 having opposed, proximal and distal ends 14, 16, and a wall structure defining an interior passageway. The distal end 16 is preformed and is substantially hook-shaped. The catheter 10 is positioned so that the distal end extends through the patient's ascending aorta 18, and into a coronary artery 20 adjacent to a stenotic obstruction 22.

As illustrated, the conventional catheter 10 is within the coronary artery ostium with the hook-shaped portion thereof within the aorta I 8. In such orientation, the catheter 10 is subject to shifting movement within the aorta. Moreover, as the catheter 10 is positioned in FIG. 1, it is very difficult to perform a PTCA procedure. As shown in phantom, a dilation balloon 23 is positioned across the stenosis 22. However, owing to the location of the catheter tip, the balloon 23 is necessarily partially within the confines ofthe catheter tip. This means that the stenotic obstruction 22 cannot be dilated to its fullest extent, which in turn means that the surgeon must withdraw the catheter tip to allow proper balloon inflation of the obstruction. This operation requires a great deal of skill and can lead to severe arterial trauma, particularly if repeated balloon dilations are necessary to reduce the stenosis.

A preferred diagnostic and guiding catheter apparatus 28 constructed in accordance with the present invention is illustrated in FIG. 2. In broad terms, the catheter apparatus 28 includes an elongated tubular body 30 having opposed, proximal and distal ends 32, 34, and an expandable distal positioning balloon structure 36 operatively coupled with the body 30 adjacent to the distal end 34. The catheter apparatus 28 also includes an expansion means for expanding the distal balloon structure 36, and structure defining a blood flow path between the aorta 18 and the coronary artery 20. When expanded, the distal balloon structure 36 provides a means for locating the distal end 34 adjacent to the coronary artery ostium, and for preventing the distal end 34 from entering the coronary artery 20. Additionally, the expansion of the distal balloon structure 36 may be controlled so that the structure 36 assumes a desired orientation. As a result, the distal end 34 may be positioned at a selected distance from the coronary artery ostium in a controlled and predictable manner by selective inflation of the balloon structure 36.

As shown in FIG. 3, tubular body 30 includes an inner sleeve 38 telescopically received within an outer sleeve 40, and a liner 42 interposed between the inner and outer sleeves 38, 40. The inner and outer sleeves 38, 40, and the liner 42 extend between the proximal and distal ends 32, 34.

Inner sleeve 38 includes wall structure presenting an exterior surface and an interior surface. As shown in FIG. 4, the exterior surface defines a trough 44 extending axially therealong between the proximal and distal ends 34, 36. A pressurizing tube passageway 46 is defined between the liner 42 and the inner sleeve exterior surface along the trough 44. Therefore, the tube passageway 46 also extends between the proximal and distal ends 32, 34.

The inner sleeve interior surface defines a main passageway 48 extending between the proximal and distal ends 32, 34. The main passageway 48 is eccentric with respect to the inner sleeve exterior surface.

The inner sleeve 38 presents a connection port 50 adjacent to the proximal end 32. The port 50 defines a port opening 52, and presents a "LUER" lock flange 54. The inner sleeve 38 also defines a tip opening 56 adjacent to the distal end 34.

The inner sleeve 38 is thus configured for receiving radio-opaque contrast from a source thereof to perform angiography. Of course, the inner sleeve 38 also is configured for receiving other material, such as medication, guide wires, and diagnostic medical devices, for insertion of the material into the patient's body. In addition, the inner sleeve 38 is configured for receiving a dilation catheter through the main passageway 50 in order to perform PTCA, stent, atherectomy, or other similar procedures where material is removed from the patient's body.

The distal end 34 presents an upper section 58, an intermediate section 60, and a tip section 62. An end of the upper section 58 abuts the proximal end 32. The intermediate section 60 extends between and abuts the upper section 58 and the tip section 62. An end of the tip section 62 is adjacent to the tip opening 56.

The distal end 34 is preformed so that the upper section 58 and the tip section 62 define an angle of between about 60°–120°, and preferably about 90°. As a result, the distal end 34 is substantially hook-shaped, and presents a classic Judkins left configuration. Of course, the distal end 34 may present other preformed configurations. In addition, the distal end 34 may also be constructed of relatively flexible material, and include a means for selectively altering the angle defined by the upper section 58 and tip section 62.

A plurality of blood flow openings 64 are defined through the inner and outer sleeve wall structures adjacent to the intermediate section 60 of the distal end 34. The blood flow openings 64, main passageway 48, and tip opening 56 thus cooperably define a blood flow path extending between the blood flow openings 64 and the tip opening 56.

The expandable distal balloon structure 36 is adhesively affixed around the tubular body 30 extending distally from the tip section 62. The distal balloon structure 36 defines a distal balloon interior 66, and includes a balloon wall structure presenting an annular contact surface 67 spaced distally from the distal end 34. When fully expanded, the distal balloon structure 36 presents a substantially toroidal shape, and is configured to maintain a maximum distance between the distal end 34 and the coronary artery ostium. The distal balloon structure 36 may also be partially expanded to position the distal end 34 relatively closer to the coronary artery ostium or minimally inside the coronary artery ostium.

The outer sleeve wall structure defines a distal balloon opening 68 adjacent to the distal balloon structure 36 communicating the distal balloon interior 66 with the pressurizing tube passageway 46. A pressurizing tube 70 is positioned within the pressurizing tube passageway 46, and extends between the proximal and distal ends 32, 34. The tube 70 presents wall structure defining a tube interior 72, and a distal tube opening 74 adjacent to the distal balloon opening 68. The tube interior 72 is thus in open communication with the distal balloon interior 66.

The proximal end of the tube 70 is configured for attachment with a source of a pressurizing fluid (not shown). The source is selectively actuated for injection of a desired amount of pressurizing fluid through the tube 70 and into the distal balloon interior 66, expanding the balloon interior 66. Therefore, pressurizing tube 70 connected with the source of fluid provides an expansion means for expanding the distal balloon structure 36.

In use, the catheter apparatus 28 is configured for introducing and removing material from a patient's body for therapeutic purposes. Referring again to FIG. 2, the catheter apparatus 28 is shown within a first blood vessel, such as the ascending aorta 18, in a position so that the contact surface 67 engages a vessel wall of the aorta 18 adjacent to the ostium of a second smaller vessel, such as the coronary artery 20. As a result, the distal end 34 is located within the aorta 18 and adjacent to the coronary artery ostium.

In a diagnostic use, radio-opaque contrast is injected into the coronary artery 20 through the main passageway 48. An X-ray image is then taken to investigate a selected area of the coronary artery 20. In a guiding use, the catheter apparatus 28 is used to guide an internal guide wire and a dilation catheter (not shown) having a dilation balloon to a stenotic obstruction 22 in the coronary artery 20. Selective inflation of the balloon structure 36 serves to move the extreme end of the distal end of the catheter tip end toward and away from the ostium in order to controllably position the tip end for proper and unimpeded positioning of a dilation balloon across the stenosis. The dilation balloon is then inflated to compress and split the obstruction 22 to increase blood flow through the coronary artery 20.

Several known methods may be used to insert the catheter apparatus 28 into the patient's cardiovascular system. As an example, after an incision is made in the patient's skin adjacent to a subcutaneous blood vessel, a hollow needle is inserted through the incision and into the blood vessel. A guide wire is then inserted through the needle, and the needle is removed. Next, the tubular body 30 is slipped over the guide wire and into the blood vessel. The guide wire is then removed.

Once inserted, the source of pressurizing fluid is actuated, and the distal balloon structure 36 is partially expanded to a desired size. The size of the partially expanded distal balloon structure 36 is such that it will not prevent blood flow through the blood vessels, such as the aorta 18, as the distal end 34 is advanced therethrough.

The distal end 34 is advanced through the patient's cardiovascular system until the tip opening 56 is adjacent to the coronary artery ostium. The distal balloon structure 36 is then expanded to assume a configuration for positioning the distal end 34 at a selected distance from the coronary artery ostium. It will be appreciated that expansion of the distal balloon structure 36 determines the spacing between the contact surface 67 and the tip opening 56. As a result, the distance between the distal end 34 and the coronary artery ostium is controlled by expanding the distal balloon structure 36 to a desired size.

The blood flow openings 64 allow blood to flow along the blood flow path between the aorta 18 and the coronary artery 20. As a result, the catheter apparatus 28 may be properly positioned for diagnostic and guiding purposes, while allowing the aorta 18 to continually supply blood to the coronary artery 20. Of course, when the dilation catheter is inserted through the catheter apparatus 28 so that the dilation balloon is adjacent to the obstruction 22, blood flow into the coronary artery 20 will be restricted. It will be appreciated that the catheter apparatus 28 advantageously minimizes the duration of the blood flow restriction.

An alternative expandable distal cuneiform balloon structure 76 is illustrated in FIG. 6. The cuneiform balloon structure 76 defines a cuneiform balloon interior 78 which is in open communication with the tube interior 72. The cuneiform balloon structure 76 upon expansion thereof provides a means for locating the tip opening 56 adjacent to the coronary artery ostium.

In addition, the cuneiform balloon structure 76 presents a plurality of spaced lobe sections, and a plurality of axially extending blood flow recesses 80 defined between adjacent lobe sections. When the tip opening 56 is positioned adjacent to the coronary artery ostium, the recesses 80 each define a blood flow path between the aorta 18 and the coronary artery 20. It will be appreciated that the cuneiform balloon structure 76 establishes a blood flow path between the aorta 18 and the coronary artery 20 apart from the blood flow openings 64. Therefore, the cuneiform balloon structure 76 may be used in addition to, or in lieu, of the blood flow openings 64 to allow the aorta 18 to continually supply blood to the coronary artery 20.

An alternative catheter apparatus 82 having an expandable biasing balloon structure 84 is illustrated in FIGS. 7 and 8. Catheter apparatus 82 is similar to catheter apparatus 28, and thus the reference numerals used in describing apparatus 28 are also used in describing apparatus 82.

Biasing balloon structure 84 is operatively coupled with tubular body 30 adjacent to the point where intermediate section 60 abuts upper section 58. The biasing balloon structure 84 defines a biasing balloon interior 86. The outer sleeve wall structure defines a biasing balloon opening 88 adjacent to the biasing balloon structure 84, and the pressurizing tube wall structure defines a second opening 90 adjacent to the biasing balloon opening 88. The biasing balloon interior 86 is thus in open communication with the tube interior 72. As a result, activation of the source of pressurizing fluid also expands the biasing balloon structure 84 in addition to the distal balloon structure 36.

The biasing balloon structure 84 is relatively less elastic than the distal balloon structure 36. As a result, when the source of pressurizing fluid is actuated, the distal balloon 36 expands prior to the biasing balloon 84.

In operation, catheter apparatus 82 is inserted into the patient's cardiovascular system in a similar manner as catheter apparatus 28. As the distal end 34 is advanced toward the coronary artery ostium, the pressurizing fluid source is actuated so that the distal balloon structure 36 expands as described with reference to catheter 28. However, the biasing balloon 84 structure may also be expanded during this placement in order to alter the configuration or effective stiffness of the distal end 34. That is to say, as the distal end is being positioned, it may be necessary change its precise hook-shaped configuration. This is accomplished by inflation of the biasing balloon structure 84 which has the effect of slightly opening the hook-shaped structure and rendering it stiffer. Thus, the surgeon may alter the shape of the hook-shaped end 34 within the patient's aorta 18 so as to achieve the most precise placement of the apparatus 82.

Once the tip opening 56 is properly positioned adjacent the coronary artery ostium, the pressurizing fluid source may again be actuated to inject additional fluid into the pressurizing tube 70 causing the biasing balloon structure 84 to expand and come into biasing contact with the opposed wall of the aorta. It will be appreciated that such expansion of the biasing balloon structure 84 biases the distal end 34 in a direction toward the coronary artery ostium, thus holding the tip opening 56 in position. By providing the biasing balloon structure 84 in combination with the positioning balloon structure 36, the surgeon can very precisely orient the end 56 relative to the ostium and stenosis 22. At the same time, this can be accomplished in aortas of different sizes without the need for catheter changeover.

The catheter apparatus 82 is illustrated in FIG. 8 showing both the positioning balloon structure and the biasing balloon structure 84 in their expanded states. The combination of these two balloon structures thus precisely orients the tip 56 relative to ostium 20 and stenosis 22. Additionally, FIG. 8 depicts a dilation catheter 23 and guiding wire 21 extending through the catheter apparatus 82. The dilation balloon of the dilation catheter is shown in position across the stenosis 22 and outside of the confines of the guiding catheter 82.

Although the present invention has been described with reference to the illustrated preferred embodiments, it is noted that variations and changes may be made, and equivalents employed herein without departing from the scope of the invention as set forth in the claims.

What is claimed is:

1. A catheter apparatus comprising:

an elongated tubular body presenting a wall structure, opposed, proximal and distal ends and blood flow openings providing fluid communication between a first blood vessel and a second blood vessel when said body is located within said first vessel with said distal end communicating with said second vessel said distal end being preformed into a hook-shape; and an expandable positioning balloon operable for locating said distal end of said body within said first blood vessel and adjacent an ostium of said second blood vessel communicating with the first blood vessel, said expandable positioning balloon operably coupled with said body adjacent said distal end thereof, and a pressurizing tube passageway defined within said tubular body and extending between the proximal end and said positioning balloon for selectively expanding said positioning balloon structure from a point adjacent said proximal end of said body in order to selectively locate said distal end relative to said ostium.

2. The apparatus as set forth in claim 1, wherein said positioning balloon structure defines a distal balloon interior space, and said pressurizing tube passageway includes a pressurizing tube adapted for connection with a source of a pressurizing fluid, said pressurizing tube including tube structure defining a tube interior and a first opening, said pressurizing tube positioned within said tube passageway and extending between said pressurizing fluid source and said positioning balloon, said tube interior being in open communication with said distal balloon interior space.

3. The apparatus as set forth in claim 2, wherein said pressurizing tube is adapted for connection with a source of liquid.

4. The apparatus as set forth in claim 2, wherein said tubular body includes an inner sleeve and an outer sleeve, said inner sleeve telescopically received within the outer sleeve, said inner and outer sleeves extending between said proximal end and said distal end.

5. The apparatus as set forth in claim 4, wherein said inner sleeve presents an exterior surface and an interior surface, said interior surface defining an axially extending main passageway, said main passageway extending between said proximal and distal ends, and being eccentric with respect to said inner sleeve exterior surface.

6. The apparatus as set forth in claim 5, wherein said inner sleeve exterior surface defines an axially extending trough, said trough extending between said proximal and distal ends, said pressurizing tube passageway being defined between said outer sleeve and said trough.

7. The apparatus as set forth in claim 2, further including a selectively expandable biasing balloon structure separate from said balloon structure operatively coupled with said tubular body for selectively altering the position of said distal end.

8. The apparatus as set forth in claim 7, said biasing balloon structure operatively coupled with said distal end and spaced from said positioning balloon structure.

9. The apparatus as set forth in claim 1, wherein said distal end is hook-shaped, and further includes an upper section, an intermediate section, and a tip section, said intermediate section extending between said upper section and said tip section, said tip section and said upper section defining an angle of between about 60°–120°.

10. The apparatus as set forth in claim 1, wherein said distal positioning balloon structure presents a generally cuneiform cross-sectional shape with a plurality of spaced lobe sections.

11. The apparatus as set forth in claim 1, wherein said distal positioning balloon structure upon expansion thereof presents a substantially toroidal shape.

12. The apparatus as set forth in claim 1, wherein said distal end includes a tip section, and said tubular body wall structure defines a blood flow opening therethrough and a tip opening adjacent said tip section, said blood flow path extending between said blood flow opening and said tip opening for permitting blood to flow between the first and second blood vessels when said second vessel is at least partially occluded by said expandable positioning balloon.

13. A catheter apparatus comprising:
an elongated tubular body presenting a wall structure, and opposed, proximal and distal ends,
said distal end configured for being located within a first blood vessel and adjacent to an ostium of a second blood vessel communicating with the first blood vessel,
an expandable positioning balloon operable for locating said distal end of said body within said first blood vessel and adjacent an ostium of said second blood vessel communicating with the first blood vessel; and
an expandable biasing balloon structure operatively coupled with said tubular body for biasing said distal end in a direction toward the second vessel ostium
said expandable biasing balloon structure, in its fully expanded state, being of smaller diameter than said first vessel.

14. The apparatus as set forth in claim 13, wherein said distal end is generally hook-shaped.

15. The apparatus as set forth in claim 13, wherein said distal end has a top and wherein said wall structure defines a blood flow opening which is in fluid communication with said top of said distal end, permitting flow of blood between said first and second blood vessels.

16. A catheter apparatus comprising:
an elongated tubular body presenting a wall structure, opposed, proximal and distal ends and blood flow openings providing fluid communication between a first blood vessel and a second blood vessel when said body is located within a first vessel with said distal end communicating with said second vessel said distal end presenting a hook-shape; and
an expandable positioning balloon operable for locating said distal end of said body within said first blood vessel and adjacent an ostium of said seconds blood vessel communicating with the first blood vessel,
said expandable positioning balloon operably coupled with said body adjacent said distal end thereof, and a pressurizing tube passageway defined within said tubular body and extending between the proximal end and said positioning balloon for selectively expanding said positioning balloon structure from a point adjacent said proximal end of said body,
said positioning balloon structure including a balloon wall structure presenting an annular contact surface for engaging said first vessel wall adjacent the second vessel ostium, said contact surface being spaced distally from said distal end of said body.

17. A catheter apparatus comprising:
an elongated tubular body presenting a wall structure and opposed, proximal and distal ends;
an expandable positioning balloon operable for locating said distal end of said body within a first blood vessel and adjacent an ostium of a second blood vessel communicating with the first blood vessel,
said expandable positioning balloon defining a distal balloon interior space and extending between the proximal end and said positioning balloon operably coupled with said body adjacent said distal end thereof and having a pressurizing tube passageway for selectively expanding said positioning balloon structure from a point adjacent said proximal end to said body in order to selectively locate said distal end relative to said ostium; and
a selectively expandable biasing balloon structure separate from positioning balloon structure and operatively coupled with said tubular body for selectively altering the position of said distal end and spaced from said positioning balloon structure,
said selectively expandable biasing balloon structure, in its fully expanded state, being of smaller diameter than said first vessel.

18. A catheter apparatus comprising:
an elongated tubular body presenting a wall structure and opposed, proximal and distal ends,
blood flow openings providing fluid communication between a first blood vessel and a second blood vessel when said body is located within said first vessel with said distal end communicating with said second vessel; and
an expandable positioning balloon operable for locating said distal end of said body within a first blood vessel and adjacent an ostium of said second blood vessel communicating with the first blood vessel,
said expandable positioning balloon operably coupled with said body adjacent said distal end thereof, and a pressurizing tube passageway defined within said tubular body and extending between the proximal end and distal balloon for selectively expanding said positioning balloon structure from a point adjacent said proximal end of said body in order to selectively locate said distal end relative to said ostium,
said distal end being hook-shaped, and further including an upper section, an intermediate section, and a tip section, said intermediate section extending between said upper section, and said tip section, said tip section and said supper section defining an angle of between about 60°–120°.

* * * * *